(12) United States Patent
Nakamura et al.

(10) Patent No.: US 8,703,162 B2
(45) Date of Patent: Apr. 22, 2014

(54) BASE MAKEUP COSMETIC AND METHOD FOR PRODUCING THE SAME

(75) Inventors: Kazuhiro Nakamura, Ashigarakami-gun (JP); Hideyasu Ishibashi, Ashigarakami-gun (JP)

(73) Assignee: FUJIFILM Corporation, Tokyo (JP)

( * ) Notice: Subject to any disclaimer, the term of this patent is extended or adjusted under 35 U.S.C. 154(b) by 0 days.

(21) Appl. No.: 13/578,766

(22) PCT Filed: Jan. 21, 2011

(86) PCT No.: PCT/JP2011/051128
§ 371 (c)(1),
(2), (4) Date: Aug. 13, 2012

(87) PCT Pub. No.: WO2011/122077
PCT Pub. Date: Oct. 6, 2011

(65) Prior Publication Data
US 2012/0315314 A1 Dec. 13, 2012

(30) Foreign Application Priority Data

Mar. 29, 2010 (JP) .................................. 2010-075550
Sep. 15, 2010 (JP) .................................. 2010-207214

(51) Int. Cl.
*A61K 8/02* (2006.01)
*A61K 8/00* (2006.01)

(52) U.S. Cl.
USPC .......................................... 424/401; 424/63

(58) Field of Classification Search
USPC .................................................. 424/401, 63
See application file for complete search history.

(56) References Cited

U.S. PATENT DOCUMENTS

2005/0158257 A1  7/2005 Ogawa et al.

FOREIGN PATENT DOCUMENTS

| JP | 7-315859 A | 12/1995 |
| JP | 8-217638 A | 8/1996 |
| JP | 9-71417 A | 3/1997 |
| JP | 11-139929 A | 5/1999 |
| JP | 2001-288038 A | 10/2001 |
| JP | 2002-146238 A | 5/2002 |
| JP | 2002-241231 A | 8/2002 |
| JP | 2003-261421 A | 9/2003 |
| JP | 2009-155209 A | 7/2009 |

OTHER PUBLICATIONS

English translation (machine translation) of JP 2002-241231, Aug. 28, 2002, pp. 1-15.*
English translation (machine translation) of JP 2001-288038, Oct. 16, 2001, pp. 1-17.*
International Search Report for PCT/JP2011/051128 dated Apr. 26, 2011, 7 pages in English and Japanese.
Written Opinion, mailed Apr. 26, 2011, issued in corresponding International Application No. PCT/JP2011/051128, 8 pages in English and Japanese.
The First Office Action, dated May 17, 2013, issued in corresponding Chinese Application No. 201180009007.4, 10 pages in English and Chinese.
The Second Office Action, dated Dec. 19, 2013, issued in corresponding CN Application No. 201180009007.4, 8 pages in English and Chinese.

* cited by examiner

*Primary Examiner* — Aradhana Sasan
(74) *Attorney, Agent, or Firm* — Sughrue Mion, PLLC

(57) ABSTRACT

A base makeup cosmetic satisfying the relationship expressed by the following Formula (1) and the relationship expressed by the following Formula (2) and exhibiting a hue angle of the cosmetic in a range of from 40° to 80°, wherein, when incident light falls on a light-receiving surface from a direction at −45° relative to the light-receiving surface, the light-receiving surface being a surface of a coating layer obtained by applying the base makeup cosmetic, (C*45) and (angle h*45) respectively represent the chroma (C*45) and hue angle (angle h*45) of reflected light in a specular reflection direction (a direction at)45°; and, when incident light falls on the light-receiving surface from a direction at −45° relative to the light-receiving surface, (C*0) and (angle h*0) respectively represent the chroma (C*0) and hue angle (angle h*0) of reflected light in a diffuse reflection direction (a direction at 0°).

(C*0)−(C*45)≤2.0                Formula (1)

|(angle h*0)−(angle h*45)|≤1.5     Formula (2)

13 Claims, No Drawings

BASE MAKEUP COSMETIC AND METHOD FOR PRODUCING THE SAME

CROSS REFERENCE TO RELATED APPLICATIONS

This application is a National Stage of International Application No. PCT/JP2011/051128 filed Jan. 21, 2011, claiming priority based on Japanese Patent Application Nos. 2010-075550 filed Mar. 29, 2010 and 2010-207214 filed Sep. 15, 2010, the contents of all of which are incorporated herein by reference in their entirety.

TECHNICAL FIELD

The present invention relates to a base makeup cosmetic and a method for producing the same.

BACKGROUND ART

It is required for base makeup cosmetics such as foundations to realize a natural finish with color tone, as well as to cover dullness of skin color (a state in which the lightness declines and the chroma of yellow increases) which is perceived with aging due to poor blood circulation or pigmentation.

As a technique aiming at improving dullness of skin color without damaging the texture of bare skin, for example, a technique of blending a blue interference mica into a foundation to enhance a sensation of clarity as well as lightness and blueness has been disclosed (see, for example, Japanese Patent Application Laid-Open (JP-A) No. 11-139929).

Further, a composite powder using metal oxide flakes and a cosmetic using the same, which have a high ultraviolet shielding ability and a high transparency with respect to visible light, and provide a favorable sensation when used, are also known (see, for example, JP-A No. 7-315859 and JP-A No. 9-71417).

However, when a conventional base makeup cosmetic is used, the gradation of color tone exhibited when the base makeup cosmetic is applied onto the skin may suddenly change when the angle of observation is changed or at a concave or convex portion of the face, to give an unnatural impression to a person who looks at the face.

SUMMARY OF INVENTION

Technical Problem

The present invention has been made in view of the above-described conventional circumstances, and aims to accomplish the following.

Namely, an object of the present invention is to provide a base makeup cosmetic, with which, when applied onto the skin, a sudden change in gradation depending on an observation angle is suppressed, and a method for producing the same.

Solution to Problem

The present invention includes the following embodiments.

[1] A method for producing a base makeup cosmetic, the method including mixing at least a colorant pigment, a pearl pigment, and an oil, so as to satisfy the relationship expressed by the following Formula (1) and the relationship expressed by the following Formula (2) and to exhibit a hue angle of the cosmetic in a range of from 40° to 80°, in which in a case of the cosmetic further including an extender pigment, a hue angle of a mixture prepared using the extender pigment, the pearl pigment, and the oil is in a range of from 50° to 80°, and in a case of the cosmetic not further including an extender pigment, a hue angle of a mixture prepared using the pearl pigment and the oil is in a range of from 50° to 80°, and a content of the pearl pigment is 7% by mass or more with respect to the total mass of the cosmetic:

$$(C^*0)-(C^*45) \leq 2.0 \quad \text{Formula (1)}$$

$$|(\text{angle } h^*0)-(\text{angle } h^*45)| \leq 1.5 \quad \text{Formula (2)}$$

wherein, when incident light falls on a light-receiving surface from a direction at −45° relative to the light-receiving surface, the light-receiving surface being a surface of a coating layer obtained by applying the base makeup cosmetic, (C*45) and (angle h*45) respectively represent the chroma (C*45) and hue angle (angle h*45) of reflected light in a specular reflection direction (a direction at 45°); and, when incident light falls on the light-receiving surface from a direction at −45° relative to the light-receiving surface, (C*0) and (angle h*0) respectively represent the chroma (C*0) and hue angle (angle h*0) of reflected light in a diffuse reflection direction (a direction at 0°).

[2] The method for producing a base makeup cosmetic according to [1], wherein the pearl pigment is a mixture of a gold pearl pigment and a red pearl pigment.

[3] The method for producing a base makeup cosmetic according to [1] or [2], wherein the extender pigment is at least one extender pigment selected from the group consisting of mica, sericite, and talc; the colorant pigment is at least one colorant pigment selected from the group consisting of yellow iron oxide, red iron oxide, black iron oxide, and titanium oxide; and the pearl pigment is at least one pearl pigment selected from the group consisting of titanium oxide-coated mica, titanium oxide-coated glass flakes, and titanium oxide-coated talc.

[4] The method for producing a base makeup cosmetic according to any one of [1] to [3], wherein a blending amount of the pearl pigment and a blending amount of the colorant pigment are adjusted.

[5] A base makeup cosmetic satisfying the relationship expressed by the following Formula (1) and the relationship expressed by the following Formula (2) and exhibiting a hue angle of the cosmetic in a range of from 40° to 80°:

$$(C^*0)-(C^*45) \leq 2.0 \quad \text{Formula (1)}$$

$$|(\text{angle } h^*0)-(\text{angle } h^*45)| \leq 1.5 \quad \text{Formula (2)}$$

wherein, when incident light falls on a light-receiving surface from a direction at −45° relative to the light-receiving surface, the light-receiving surface being a surface of a coating layer obtained by applying the base makeup cosmetic, (C*45) and (angle h*45) respectively represent the chroma (C*45) and hue angle (angle h*45) of reflected light in a specular reflection direction (a direction at 45°); and, when incident light falls on the light-receiving surface from a direction at −45° relative to the light-receiving surface, (C*0) and (angle h*0) respectively represent the chroma (C*0) and hue angle (angle h*0) of reflected light in a diffuse reflection direction (a direction at 0°).

[6] The base makeup cosmetic according to [5] satisfying the relationship expressed by the following Formula (1') and the relationship expressed by the following Formula (2').

$$(C^*0)-(C^*45) \leq 1.5 \qquad \text{Formula (1')}$$

$$|(\text{angle } h^*0)-(\text{angle } h^*45)| \leq 1.5 \qquad \text{Formula (2')}$$

[7] The base makeup cosmetic according to [5] or [6], satisfying the relationship expressed by the following Formula (1a) and the relationship expressed by the following Formula (2a).

$$(C^*0)-(C^*45) \leq 1.0 \qquad \text{Formula (1a)}$$

$$|(\text{angle } h^*0)-(\text{angle } h^*45)| \leq 1.0 \qquad \text{Formula (2a)}$$

[8] The base makeup cosmetic according to any one of [5] to [7], satisfying the relationship expressed by the following Formula (1b).

$$-5 \leq (C^*0)-(C^*45) \leq 0 \qquad \text{Formula (1b)}$$

[9] The base makeup cosmetic according to any one of [5] to [8], satisfying the relationship expressed by the following Formula (1c).

$$|(C^*0)-(C^*45)| \leq 1.5 \qquad \text{Formula (1c)}$$

[10] The base makeup cosmetic according to any one of [5] to [9], satisfying the relationship expressed by the following Formula (3):

$$(L^*45)-(L^*0) \geq 5.0 \qquad \text{Formula (3)}$$

wherein, when incident light falls on the light-receiving surface from a direction at −45° relative to the light-receiving surface, (L*45) and (L*0) respectively represent the lightness (L*45) of reflected light in the specular reflection direction (the direction at 45°), and the lightness (L*0) of reflected light in the diffuse reflection direction (the direction at 0°).

[11] The base makeup cosmetic according to any one of [5] to [10], including at least a colorant pigment, a pearl pigment, and an oil, in which in a case of further including an extender pigment, a hue angle of a mixture prepared using the extender pigment, the pearl pigment, and the oil is in a range of from 50° to 80°, and in a case of not further including an extender pigment, a hue angle of a mixture prepared by using the pearl pigment and the oil is in a range of from 50° to 80°, and a content of the pearl pigment is 7% by mass or more with respect to the total mass of the cosmetic.

[12] The base makeup cosmetic according to [11], wherein the pearl pigment is a mixture of a gold pearl pigment and a red pearl pigment.

[13] The base makeup cosmetic according to [11] or [12], wherein the extender pigment is at least one extender pigment selected from the group consisting of mica, sericite, and talc; the colorant pigment is at least one colorant pigment selected from the group consisting of yellow iron oxide, red iron oxide, black iron oxide, and titanium oxide; and the pearl pigment is at least one pearl pigment selected from the group consisting of titanium oxide-coated mica, titanium oxide-coated glass flakes, and titanium oxide-coated talc.

[14] The base makeup cosmetic according to any one of [5] to [13] being a powder foundation, a liquid foundation, or a creamy foundation.

Advantageous Effects of Invention

According to the present invention, it is possible to provide a base makeup cosmetic, with which, when applied onto the skin, a sudden change in gradation depending on an observation angle is suppressed, and a method for producing the same.

DESCRIPTION OF EMBODIMENTS

[Base Makeup Cosmetic]

The base makeup cosmetic of the present invention (hereinafter, referred to as the "cosmetic" as appropriate) is a base makeup cosmetic in which, when incident light falls on a light-receiving surface from a direction at −45° relative to the light-receiving surface, the light-receiving surface being a surface of a coating layer, the chroma (C*45) and hue angle (angle h*45) of reflected light in a specular reflection direction (a direction at 45°) and the chroma (C*0) and hue angle (angle h*0) of reflected light in the diffuse reflection direction (a direction at 0°) satisfy the relationship expressed by the following Formula (1) and the relationship expressed by the following Formula (2), and in which a hue angle of the cosmetic is in a range of from 40° to 80°.

$$(C^*0)-(C^*45) \leq 2.0 \qquad \text{Formula (1)}$$

$$|(\text{angle } h^*0)-(\text{angle } h^*45)| \leq 1.5 \qquad \text{Formula (2)}$$

The chroma, the hue angle, and the lightness in the present invention are those obtained in accordance with the L*a*b* color system which are standardized by CIE (the International Commission of Illumination) in 1976 and specified by JIS Z 8729.

In the cosmetic of the present invention, the relationships expressed by Formula (1) and Formula (2) specify the variations in chroma and hue angle, respectively, in the case of varying the light-receiving angle from 0° to 45°. By setting the variations to be within the ranges of Formula (1) and Formula (2), a sudden change in gradation depending on an observation angle is suppressed when the cosmetic of the present invention is applied onto the skin.

In this specification, as to the formation of a coating layer whose surface is deemed as the light-receiving surface, a coating layer which is formed, as described below, by using the cosmetic of the present invention is used, and as to the measurement values of chroma, hue angle, and lightness, the measurement values which are measured using, as the light-receiving surface, the surface of the coating layer are used.

—Formation of Coating Layer—

A cosmetic which is the object to be measured is evenly applied onto a commercially available skin color sheet made of resin (BIO SKIN PLATE, manufactured by Beaulax Co., Ltd.); standard skin color (item number: BIO)) in an application amount of 4.5 mg for an area of a rectangle of 3 cm×5 cm (0.3 g/cm²), to prepare a measurement sample having a coating layer.

—Measurement of Chroma, Hue Angle, and Lightness—

With regard to the measurement sample thus prepared, using a goniospectrophotometer color measurement system GCMS-3B (manufactured by Murakami Color Research Laboratory), the lightness L*, chroma C*, and hue angle, angle h, under a C light source are obtained, by allowing incident light to fall on from a direction at −45° and measuring the reflectance at an angle from −70° to 70° at 5° intervals, with respect to the wavelength region of from 390 nm to 730 nm at 10 nm intervals.

In the cosmetic of the present invention, it is preferable that the above-described (C*45), (angle h*45), (C*0), and (angle h*0) satisfy the relationship expressed by the following Formula (1') and the relationship expressed by the following Formula (2').

$$(C^*0)-(C^*45) \leq 1.5 \qquad \text{Formula (1')}$$

$$|(\text{angle } h^*0)-(\text{angle } h^*45)| \leq 1.5 \qquad \text{Formula (2')}$$

In the cosmetic of the present invention, it is more preferable that the above-described (C*45), (angle h*45), (C*0), and (angle h*0) satisfy the relationship expressed by the following Formula (1a) and the relationship expressed by the following Formula (2b).

$$(C*0)-(C*45) \leq 1.0 \quad \text{Formula (1a)}$$

$$|(\text{angle } h*0)-(\text{angle } h*45)| \leq 1.0 \quad \text{Formula (2a)}$$

Concerning the chroma shown by the cosmetic of the present invention, it is preferable that the above-described (C*45) and (C*0) satisfy the relationship expressed by the following Formula (1b), and it is more preferable that the above-described (C*45) and (C*0) satisfy the relationship expressed by the following Formula (1c).

$$-5 \leq (C*0)-(C*45) \leq 0 \quad \text{Formula (1b)}$$

$$|(C*0)-(C*45)| \leq 1.5 \quad \text{Formula (1c)}$$

Further, in a preferable embodiment of the cosmetic of the present invention, when incident light falls on the light receiving surface from a direction at −45° relative to the light-receiving surface, the lightness (L*45) of reflected light in the specular reflection direction (the direction at 45°), and the lightness (L*0) of reflected light in the diffuse reflection direction (the direction at 0°) satisfy the relationship expressed by the following Formula (3).

$$(L*45)-(L*0) \geq 5.0 \quad \text{Formula (3)}$$

In the cosmetic of the present invention, as shown in Formula (3) above, a sudden change in gradation depending on an observation angle is suppressed, also in the range in which the lightness is great. Further, in a case in which the relationship expressed by Formula (3) above is satisfied, a good gloss is exhibited.

Moreover, the cosmetic of the present invention, as a whole, should have a hue angle of from 40° to 80°, and it is more preferable that the hue angle is in a range of from 50° to 70°. When the hue angle is within the range of from 40° to 80°, the suppression effects by the cosmetic of the present invention on a sudden change in gradation may be most directly exhibited. Here, the term "within the range of the hue angle of the whole cosmetic" indicates that the values measured as described above as the (angle h*45) and (angle h*0) according to the present invention are each within the range of from 40° to 80°.

In the cosmetic of the present invention, in order to satisfy the relationship expressed by Formula (1) and the relationship expressed by Formula (2) above and to adjust the hue angle of the cosmetic to be within the range of from 40° to 80°, for example, the kind and content of the pigments and additives, which are incorporated in the cosmetic, may be adjusted. In a more preferable embodiment, for example, the kind and content of the colorant pigment and the pearl pigment, which are contained as pigments, are adjusted.

In a case in which the cosmetic of the present invention is a powdery cosmetic or a cosmetic obtained by solidifying powder, such as a powder foundation, pressed powder, or loose powder, the cosmetic contains at least an extender pigment, a colorant pigment, 10% by mass or more of a pearl pigment, and an oil. In this case, the hue angle of a mixture prepared by using the extender pigment, the pearl pigment and the oil should be within the range of from 50° to 80°, and it is more preferable that the hue angle of the mixture is within the range of from 60° to 80°.

Further, in a case in which the cosmetic of the present invention is a liquid or paste-like cosmetic, such as a liquid foundation, a creamy foundation, or a makeup base, an extender pigment is not an essential component, and the cosmetic contains at least a colorant pigment, 7% by mass or more of a pearl pigment, and an oil. In this case, the hue angle of a mixture prepared by using the pearl pigment and the oil should be within the range of from 50° to 80°, and it is more preferable that the hue angle of the mixture is within the range of from 60° to 80°.

In the above-described mixture according to the present invention, in order to adjust the hue angle to be within the range of from 50° to 80°, for example, the kind and content of the components, which are contained in the mixture and are used for preparing the mixture, may be adjusted.

The preparation of the mixture using an extender pigment, a pearl pigment, and an oil, and the measurement of a hue angle are conducted by forming a mixture using the extender pigment, the pearl pigment, and the oil, which are incorporated in the cosmetic of the present invention, and measuring a hue angle using the obtained mixture.

In this specification, the measurement value of the hue angle of the mixture is a measurement value obtained in accordance with the following preparation of a mixture and method of measuring a hue angle.

—Preparation of Mixture—

Based on the kinds and the amounts contained in the cosmetic which is an object to be measured, the pearl pigment, the oil, and the extender pigment in the case of containing an extender pigment are weighed out, and these components are mixed using a HENSCHEL mixer until the mixture is uniform, thereby preparing a mixture.

—Method of Measuring Hue Angle—

A glass substrate (3 cm×5 cm) is prepared which has, on one surface (front face), a transparent adhesive layer formed by using a commercially available acrylic adhesive sheet (for laminating deflecting plates) and has the other surface (rear face) painted out with a black ink until the rear face does not reflect light at all.

The obtained mixture is weighed so as to give a coating amount of 4.5 mg (0.3 g/cm$^2$), and the mixture is evenly applied onto the surface of the above glass plate, using a index finger wearing a latex glove, in the inside of a frame made of a transparent plastic sheet hollowed out in a rectangle having the size described above. With regard to the glass plate that has been applied with the mixture, using an apparatus in which an integrating sphere (ISR-2200, manufactured by Shimazu Corporation) is attached to a spectrophotometer (UV-2550, manufactured by Shimazu Corporation), the spectral reflectance is measured at a wavelength of from 380 nm to 780 nm at 1 nm intervals under the conditions of diffuse reflection measurement, to calculate the hue angle, angle h, of reflected light when assuming a C light source.

In a case in which the cosmetic of the present invention contains an extender pigment and two or more types of pearl pigments, it is preferable that the above hue angle obtained by the measurement with regard to the mixture including the extender pigment and the two or more pearl pigments is within the range of from 50° to 80°.

In the cosmetic of the present invention, when the content of the pearl pigment and the hue angle shown by the mixture are each adjusted to be within the respective ranges according to the present invention, the relationship expressed by Formula (1) and the relationship expressed by Formula (2) above can be satisfied.

The extender pigment, the colorant pigment, the pearl pigment, and the oil, which may be incorporated in the cosmetic of the present invention, are further described.

<Extender Pigment>

In the cosmetic of the present invention, the term "extender pigment" means a pigment that does not substantially contribute to the adjustment of hue. In a case in which the cosmetic of the present invention is a powdery cosmetic or a cosmetic obtained by solidifying powder, such as a powder foundation, pressed powder, or loose powder, the extender pigment is incorporated in the cosmetic as the main component.

Examples of the extender pigment include mica, synthetic bronze mica, talc, kaolin, mica, sericite, magnesium carbonate, calcium carbonate, silicic anhydride, aluminium oxide, and barium sulfate.

A commercially available product may be used as the extender pigment, and examples thereof include SERICITE FSE (manufactured by Sanshin Mining Ind. Co., Ltd.), TALC JA-46R (manufactured by Asada Milling Co., Ltd.), and synthetic bronze mica PDM series (manufactured by TOPY INDUSTRIES, LTD.).

Regarding the particle diameter of the extender pigment, the average primary particle diameter is preferably from 1 μm to 100 μm, and more preferably from 5 μm to 80 μm.

The particle diameter of the pigment in the present invention can be measured using various commercially available measuring apparatuses (for example, a laser diffraction/scattering particle size distribution analyzer LMS-30 (manufactured by SEISHIN ENTERPRISE CO., LTD.) or the like) based on the principle of laser light scattering, after preparing a solvent dispersion of a specific concentration which contains a pigment that is the object to be measured.

The content of the extender pigment in the cosmetic of the present invention may differ depending on the form of the cosmetic, and it is preferable that the extender pigment is contained at an optimum amount depending on the form of the cosmetic. For example, in the case of a powdery cosmetic or a cosmetic obtained by solidifying powder, such as a powder foundation or the like, the content of the extender pigment is preferably from 50% by mass to 90% by mass with respect to the total mass of the cosmetic.

In the case of a liquid or paste-like cosmetic, such as a liquid foundation or the like, the extender pigment is not necessarily contained as an essential component, and the content of the extender pigment is preferably from 0% by mass to 30% by mass with respect to the total mass of the cosmetic.

<Colorant Pigment>

In the cosmetic of the present invention, the term "colorant pigment" means a pigment which contributes to the adjustment of hue and is other than a pearl pigment.

Examples of the colorant pigment include inorganic pigments such as yellow iron oxide, red iron oxide, black iron oxide, titanium oxide, red iron oxide, ultramarine blue, or Prussian blue, and those containing an organic dye including certified dyes such as Red No. 106, Red No. 201, Red No. 202, Red No. 203, Red No. 226, Yellow No. 4, Yellow No. 5, or Yellow No. 401, a cochineal dye, calcium lakes thereof, aluminum lakes thereof, and calcium aluminum lakes thereof.

Further, examples include white pigments such as titanium oxide or zinc oxide. These white pigments may also function as a masking agent for stains, freckles, or the like, or as an agent for preventing ultraviolet rays.

As to the shape and particle diameter of these pigments, for example, regarding the white pigments, those having a spherical shape and having a particle diameter of from several nm to several hundred nm are preferably used; and regarding the iron oxides, those having a spherical shape or a needle-like shape and having a particle diameter of from several nm to several hundred nm are preferably used.

The addition amounts of the pigments are adjusted as appropriate such that the color tone of the foundation as a whole becomes a desired color tone.

<Pearl Pigment>

In the present invention, the term "pearl pigment" means a pigment which contributes to the adjustment of hue and has a pearly luster.

Examples of the pearl pigment include titanium oxide-coated mica (titanated mica), titanium oxide-coated glass flakes, and titanium oxide-coated talc. Further, pearl pigments having plural titanium oxide-coated layers, or having silicone oxide coating, or the like may be used preferably.

As the pearl pigment, a commercially available product can also be used, and examples thereof include RONAFLAIR BALANCE GOLD, TRANS PRISMA RED, and TIMIRON SUPER SILK MP-1005 (manufactured by MERK) and FLAMENCO series (manufactured by BASF).

The pearl pigment incorporated in the cosmetic of the present invention is preferably a mixture of a gold pearl pigment and a red pearl pigment.

Regarding the particle diameter of the pearl pigment, the average primary particle diameter is preferably from 0.5 μm to 100 μm, and more preferably from 1 μm to 80 μm.

The pearl pigment in the present invention should be 7% by mass or more with respect to the total mass of the cosmetic, preferably 10% by mass or more with respect to the total mass of the cosmetic, preferably from 10% by mass to 50% by mass with respect to the total mass of the cosmetic, more preferably from 13% by mass to 50% by mass with respect to the total mass of the cosmetic, more preferably from 14% by mass to 50% by mass with respect to the total mass of the cosmetic, more preferably from 15% by mass to 50% by mass with respect to the total mass of the cosmetic, and even more preferably from 18% by mass to 40% by mass with respect to the total mass of the cosmetic. The pearl pigment incorporated in the cosmetic of the present invention may be one type of pearl pigment or two or more types of pearl pigments.

The combination of the extender pigment, the colorant pigment, and the pearl pigment is determined so as to satisfy the relationship expressed by Formula (1) and the relationship expressed by Formula (2) above.

A preferable example of a combination of these pigments is a combination in which the extender pigment is at least one pigment selected from the group consisting of mica, sericite, and talc, the colorant pigment is at least one pigment selected from the group consisting of yellow iron oxide, red iron oxide, black iron oxide, and titanium oxide, and the pearl pigment is at least one pigment selected from the group consisting of titanium oxide-coated mica (titanated mica), titanium oxide-coated glass flakes, and titanium oxide-coated talc.

<Oil>

Examples of the oil include oil components generally used in cosmetics, examples of thereof including liquid paraffin, Vaseline, paraffin wax, squalane, beeswax, carnauba wax, olive oil, lanolin, higher alcohols, fatty acids, higher fatty acids, ester oils, ceresin, microcrystalline wax, candelilla wax, diglyceride, triglyceride, silicone oil, perfluoropolyether, perfluorodecalin, perfluorooctane, jojoba oil, octyldodecyl myristate, and neopentylglycol dioctanate.

As necessary, besides the above-described extender pigments, colorant pigments, pearl pigments, and oils, one or more components that are blended into ordinary cosmetics may be blended into the cosmetic of the present invention, as far as the effects of the invention are not impaired; and examples of the one or more additional components include a surfactant, a water-soluble polymer, powder other than the pigments described above, a moisturizing agent, an antiseptic, a drug, an ultraviolet absorbent, a coloring matter, an inorganic salt or organic salt, a perfume, a chelating agent, a pH adjusting agent, and water.

Examples of the surfactant include surfactants that are generally used in cosmetics, examples thereof including nonionic surfactants, for example, polyoxyethylene alkyl ether, polyoxyethylene fatty acid ester, polyoxyethylene sorbitan fatty acid ester, glycerin fatty acid ester, polyglycerin fatty acid ester, polyoxyethylene glycerin fatty acid ester, polyoxyethylene hydrogenated castor oil, polyoxyethylene sorbitol fatty acid ester, or the like; anionic surfactants represented by fatty acid soaps such as sodium stearate or triethanolamine palmitate; cationic surfactants; and amphoteric surfactants.

Examples of the water-soluble polymer include water-soluble polymers that are generally used in cosmetics, examples thereof including carboxymethylcellulose, methylcellulose, hydroxymethylcellulose, polyvinyl alcohol, polyvinyl pyrrolidone, gum tragacanth, carrageenen, locust bean gum, dextrin, dextrin fatty acid esters, carboxyvinyl polymers, xanthan gum, gelatin, sodium alginate, and gum arabic.

Examples of the moisturizing agent include moisturizing agents that are generally used in cosmetics, examples thereof including sorbitol, xylitol, glycerin, maltitol, propylene glycol, 1,3-butylene glycol, 1,4-butylene glycol, sodium pyrrolidone carboxylate, lactic acid, sodium lactate, and polyethylene glycol.

Examples of the antiseptic include antiseptics that are generally used in cosmetics, examples thereof including p-oxybenzoic acid alkyl ester, sodium benzoate, and potassium sorbate.

Examples of the drug that may be used include drugs that are generally used in cosmetics, examples thereof including vitamins, herbal drugs, antiphlogistic agents, and germicides.

Examples of the ultraviolet absorbent include ultraviolet absorbents that are generally used in cosmetics, examples thereof including p-aminobenzoic acid-based ultraviolet absorbents, anthranyl-based ultraviolet absorbents, salicylic acid-based ultraviolet absorbents, cinnamic acid-based ultraviolet absorbents, and benzophenone-based ultraviolet absorbents.

Examples of the coloring matter include coloring matters that are generally used in cosmetics, examples thereof including tar dyes, such as Red No. 3, Red No. 104, Red No. 106, Red No. 201, Red No. 202, Red No. 204, Red No. 205, Red No. 220, Red No. 226, Red No. 227, Red No. 228, Red No. 230, Red No. 401, Red No. 505, Yellow No. 4, Yellow No. 5, Yellow No. 202, Yellow No. 203, Yellow No. 204, Yellow No. 401, Blue No. 1, Blue No. 2, Blue No. 201, Blue No. 404, Green No. 3, Green No. 201, Green No. 204, Green No. 205, Orange No. 201, Orange No. 203, Orange No. 204, Orange No. 206, Orange No. 207, or the like; and natural dyes such as carminic acid, laccaic acid, brazilin, or crocin.

Examples of the inorganic salt or organic salt include alkali metal salts, alkaline earth metal salts, or aluminum salts of an inorganic acid such as hydrochloric acid, sulfuric acid, or nitric acid; an oxycarboxylic acid such as citric acid, tartaric acid, lactic acid, or malic acid; a carboxylic acid such as formic acid, acetic acid, or sorbic acid; or an aromatic carboxylic acid such as salicylic acid or benzoic acid.

Specific examples of a preferable inorganic salt or organic salt include potassium sulfate, sodium sulfate, magnesium sulfate, aluminum sulfate, potassium nitrate, sodium nitrate, magnesium nitrate, aluminum nitrate, calcium nitrate, potassium chloride, magnesium chloride, sodium chloride, calcium chloride, aluminum chloride, potassium carbonate, sodium carbonate, aluminum carbonate, potassium acetate, sodium acetate, calcium acetate, magnesium acetate, sodium formate, potassium formate, magnesium formate, sodium citrate, sodium tartrate, potassium sorbate, sodium sorbate, sodium salicylate, potassium benzoate, and sodium benzoate; and particularly, potassium sulfate, magnesium sulfate, potassium chloride, magnesium chloride, aluminum chloride, sodium citrate, sodium tartrate, potassium sorbate, sodium salicylate, and sodium benzoate are preferable.

Such inorganic salt or organic salt may be blended, in a salt state, into the cosmetic of the present, but a corresponding acid substance and a basic substance may be added in a stoichiometric amount necessary for forming a salt, during the production of the cosmetic of the present invention. Further, water may be blended in an arbitrary amount.

The cosmetic of the present invention may be used in the form of, for example, a foundation, such as a powder foundation, a creamy foundation, a liquid foundation, or a concealer, a makeup base, face powder, or the like.

[Method for Producing Base Makeup Cosmetic]

The method for producing a base makeup cosmetic according to the present invention (hereinafter, may also be referred to as the "production method of the present invention" as appropriate), is a method for producing a base makeup cosmetic, the method including a process of mixing at least a colorant pigment, a pearl pigment, and an oil, so as to satisfy the relationship expressed by Formula (1) above and the relationship expressed by Formula (2) above and to exhibit a hue angle of the cosmetic of from 40° to 80°, in which, in a case of the cosmetic including an extender pigment, a hue angle of a mixture prepared using the extender pigment, the pearl pigment, and the oil is in a range of from 50° to 80°, and, in a case of the cosmetic not including an extender pigment, a hue angle of a mixture prepared using the pearl pigment and the oil is in a range of from 50° to 80°, and the content of the pearl pigment is 7% by mass or more with respect to the total mass of the cosmetic.

In the production method of the present invention, examples of a method to satisfy the relationship expressed by Formula (1) and the relationship expressed by Formula (2) above and to adjust a hue angle of the cosmetic to be within the range of from 40° to 80° include a method in which the kind and blending amount of the pigments and additives which are incorporated in the cosmetic are adjusted. More preferable examples include a method in which the kind and blending amount of the colorant pigment and the pearl pigment are adjusted.

Further, as a method to adjust the hue angle of the mixture to be within the range of from 50° to 80°, for example, the kind and content of the pigment and the oil, which are used for preparing the mixture, may be adjusted.

For the details on the kind and content of the extender pigment, the colorant pigment, the oil, and the arbitrary usable one or more additional components, which may be used in the production method of the present invention, the same contents described in the explanation of the cosmetic of the present invention can be applied.

Mixing of the respective components in the production method of the present invention may be carried out by mixing the components to be incorporated in the cosmetic, using a HENSCHEL mixer or the like, until the hue of the mixture is uniform.

In an embodiment concerning the mixing of the components, all of the extender pigment, the colorant pigment, the pearl pigment, the oil, and the one or more additional components that may be arbitrary used are mixed simultaneously, or in another embodiment, components such as the extender pigment, the colorant pigment, the pearl pigment, the oil, and the like are mixed, and then other components, such as a perfume, an antiseptic, or a beauty ingredient, are added and further mixed.

Further, the mixture formed from the components which constitute the cosmetic may be crashed, using a hammer mill or the like, and then the resultant may be pressed to a dish using a press machine or the like, whereby a powder foundation can be obtained.

Furthermore, in the case of a liquid or paste-like cosmetic such as a liquid foundation or a creamy foundation, the mixture after mixing can be used as a foundation without being subjected to any processing.

EXAMPLES

Hereinafter, the present invention will be described in detail with reference to Examples. However, it should be construed that the invention is by no means limited thereto. Note that, unless otherwise specifically stated, the term "parts" is based on mass.

Examples 1 to 11, and Comparative Examples 1 to 6

<Preparation of Powder Foundation>

The components of each of the phase A and the phase B, which are shown in Table 1 (the numeric values indicating part(s) by mass) described below, were separately weighed out, and were sufficiently mixed using a HENSCHEL mixer, until a uniform hue was obtained, whereby powder foundations of Examples 1 to 11, and Comparative Examples 1 to 6 were prepared.

Further, the extender pigments (sericite and talc) and the pearl pigment(s) which were used in the phase A and the two types of oils used in the phase B in Examples 1 to 11 and Comparative Examples 1 to 6 were mixed in a manner substantially similar to that in the preparation of the powder foundation in Example 1, whereby mixtures each corresponding to the respective Examples and Comparative Examples were prepared.

A glass substrate (3 cm×5 cm) was prepared, which has, on one surface (front face), a transparent adhesive layer formed by using a commercially available acrylic adhesive sheet (for laminating deflecting plates) and has the other surface (rear face) painted out with a black ink until the rear face does not reflect light at all.

On the surface of the above glass plate, each of the obtained mixtures was evenly applied so as to give a coating amount of 4.5 mg (0.3 g/cm$^2$) for an area of a rectangle of 3 cm×5 cm, and with regard to the glass plate that has been applied with the mixture, the spectral reflectance was measured at a wavelength of from 380 nm to 780 nm at 1 nm intervals under the conditions of diffuse reflection measurement, using an apparatus in which an integrating sphere (ISR-2200, manufactured by Shimazu Corporation) was attached to a spectrophotometer (UV-2550, manufactured by Shimazu Corporation), to calculate the hue angle, angle h, of reflected light when assuming a C light source.

The obtained results are also shown in Table 1.

TABLE 1

| | Material | Example 1 | Example 2 | Example 3 | Example 4 | Example 5 | Example 6 |
|---|---|---|---|---|---|---|---|
| Phase A | Extender pigment: Sericite *[1] | 40.543 | 41.444 | 33.785 | 27.028 | 43.921 | 40.543 |
| | Extender pigment; Talc *[2] | 18.244 | 18.650 | 15.203 | 12.163 | 19.765 | 18.244 |
| | Colorant pigment: Titanium oxide *[3] | 9.009 | 9.009 | 9.009 | 9.009 | 9.009 | 9.009 |
| | Colorant pigment: Iron oxide (yellow) *[4] | 1.802 | 0.901 | 1.802 | 1.802 | 1.802 | 1.802 |
| | Colorant pigment: Iron oxide (red) *[5] | 0.541 | 0.270 | 0.541 | 0.541 | 0.541 | 0.541 |
| | Colorant pigment: Iron oxide (black) *[6] | 0.270 | 0.135 | 0.270 | 0.270 | 0.270 | 0.270 |
| | Pearl pigment (gold) *[7] | 13.064 | 13.064 | 19.596 | 26.127 | 9.798 | 15.676 |
| | Pearl pigment (red) *[8] | 6.532 | 6.532 | 9.798 | 13.064 | 4.899 | 3.919 |
| | Pearl pigment (silver) *[9] | | | | | | |
| Phase B | Dimethicone (and) Trimethyl siloxy silicate *[10] | 2.988 | 2.988 | 2.988 | 2.988 | 2.988 | 2.988 |
| | Dimethicone (20) *[11] | 7.007 | 7.007 | 7.007 | 7.007 | 7.007 | 7.007 |
| Hue angle, angle h, of reflected light of the mixture (pearl pigment + extender pigment + oil) | | 67 | 67 | 67 | 67 | 67 | 78 |

| | Material | Example 7 | Example 8 | Example 9 | Example 10 | Example 11 | Comparative Example 1 |
|---|---|---|---|---|---|---|---|
| Phase A | Extender pigment: Sericite *[1] | 40.543 | 27.929 | 41.350 | 40.543 | 47.300 | 54.958 |
| | Extender pigment; Talc *[2] | 18.244 | 12.568 | 18.608 | 18.244 | 21.285 | 24.731 |
| | Colorant pigment: Titanium oxide *[3] | 9.009 | 9.009 | 9.009 | 9.009 | 9.009 | 9.009 |
| | Colorant pigment: Iron oxide (yellow) *[4] | 1.802 | 0.901 | 0.901 | 1.802 | 1.802 | 0.901 |
| | Colorant pigment: Iron oxide (red) *[5] | 0.541 | 0.270 | 0.270 | 0.541 | 0.541 | 0.270 |
| | Colorant pigment: Iron oxide (black) *[6] | 0.270 | 0.135 | 0.270 | 0.270 | 0.270 | 0.135 |
| | Pearl pigment (gold) *[7] | 11.757 | 26.127 | 13.064 | 9.798 | 6.532 | |
| | Pearl pigment (red) *[8] | 7.838 | 13.064 | 6.532 | 9.798 | 3.266 | |
| | Pearl pigment (silver) *[9] | | | | | | |
| Phase B | Dimethicone (and) Trimethyl siloxy silicate *[10] | 2.988 | 2.988 | 2.988 | 2.988 | 2.988 | 2.988 |
| | Dimethicone (20) *[11] | 7.007 | 7.007 | 7.007 | 7.007 | 7.007 | 7.007 |
| Hue angle, angle h, of reflected light of the mixture (pearl pigment + extender pigment + oil) | | 61 | 67 | 67 | 56 | 67 | 89 |

| | Material | Comparative Example 2 | Comparative Example 3 | Comparative Example 4 | Comparative Example 5 | Comparative Example 6 |
|---|---|---|---|---|---|---|
| Phase A | Extender pigment: Sericite *[1] | 40.543 | 40.543 | 40.543 | 40.543 | 36.069 |
| | Extender pigment; Talc *[2] | 18.244 | 18.244 | 18.244 | 18.244 | 16.231 |
| | Colorant pigment: Titanium oxide *[3] | 9.009 | 9.009 | 9.009 | 9.009 | 9.009 |
| | Colorant pigment: Iron oxide (yellow) *[4] | 1.802 | 1.802 | 1.802 | 1.802 | 7.208 |
| | Colorant pigment: Iron oxide (red) *[5] | 0.541 | 0.541 | 0.541 | 0.541 | 1.622 |
| | Colorant pigment: Iron oxide (black) *[6] | 0.270 | 0.270 | 0.270 | 0.270 | 0.270 |

TABLE 1-continued

|  |  |  |  |  |  |  |
|---|---|---|---|---|---|---|
| | Pearl pigment (gold) *[7] | 17.636 | 19.596 | | | |
| | Pearl pigment (red) *[8] | 1.960 | | 19.596 | | |
| | Pearl pigment (silver) *[9] | | | | 19.596 | 19.596 |
| Phase B | Dimethicone (and) Trimethyl siloxy silicate *[10] | 2.988 | 2.988 | 2.988 | 2.988 | 2.988 |
| | Dimethicone (20) *[11] | 7.007 | 7.007 | 7.007 | 7.007 | 7.007 |
| Hue angle, angle h, of reflected light of the mixture (pearl pigment + extender pigment + oil) | | 89 | 91 | 15 | −98 | −98 |

*[1] OTS-2 SERICITE FSE (manufactured by DAITO KASEI KOGYO CO., LTD.)
*[2] OTS-2 TALK JA-46R (manufactured by DAITO KASEI KOGYO CO., LTD.)
*[3] OTS-2 TIO$_2$ CR-50 (manufactured by DAITO KASEI KOGYO CO., LTD.)
*[4] OTS-2 YELLOW LLXLO (manufactured by DAITO KASEI KOGYO CO., LTD.)
*[5] OTS-2 RED R-516L (manufactured by DAITO KASEI KOGYO CO., LTD.)
*[6] OTS-2 BLACK BL-100 (manufactured by DAITO KASEI KOGYO CO., LTD.)
*[7] RONAFLAIR BALANCE GOLD (manufactured by Merck)
*[8] TIMIRON SPLENDID RED (manufactured by Merck)
*[9] TIMIRON SUPER SILK MP-1005 (manufactured by Merck)
*[10] DC593 (manufactured by Dow Corning Toray Co., Ltd.)
*[11] SH200C-20CS (manufactured by Dow Corning Toray Co., Ltd.)

<Application of Foundation>

Each of the powder foundations of Examples 1 to 11 and Comparative Examples 1 to 6 were evenly applied onto a commercially available skin color sheet made of resin (BIO SKIN PLATE, manufactured by Beaulax Co., Ltd.); standard skin color (item number: BIO)) in an application amount of 4.5 mg for an area of a rectangle of 3 cm×5 cm (0.3 g/cm$^2$), whereby samples for evaluation were prepared.

<Evaluation of Foundation>

1. Color Measurement

Each of the samples obtained as described above was subjected to color measurement using a goniospectrophotometer color measurement system GCMS-3B (manufactured by Murakami Color Research Laboratory), by allowing the incident light to fall on from a direction at −45° and measuring the reflectance at from −70° to 70° at 5° intervals, with respect to the wavelength region of from 390 nm to 730 nm at 10 nm intervals, whereby the lightness L*, the chroma C*, and the hue angle, angle h, under a C light source were obtained.

As the numeric values representing the average color, the lightness L (L*45°), chroma C* (C*45°), and hue angle (angle h45°) at a direction of 45° are shown in Table 2.

Further, the changes in the chroma C*, the hue angle, angle h, and the lightness L*, when observed from the front (0°) direction and when observed from the oblique (45°) direction, are considered to be the differences between the respective values, and are expressed by (L*(0°−45°)), (C*(0°−45°)), and (angle h*(0°−45°)), which are shown in Table 2.

As the value of (C*(0°−45°)) gets closer to 0, it indicates that the change in chroma due to the observation angle between 45° and 0° is smaller. That the value of (C*(0°−45°)) is 2.0 or less means that the relationship expressed by Formula (1) is satisfied.

As the value of (angle h(0°−45°)) gets closer to 0, it indicates that the change in hue angle due to the observation angle between 45° and 0° is smaller. That the absolute value of (angle h(0°−45°)) is 1.5 or less means that the relationship expressed by Formula (2) is satisfied.

Further, the value of (L*(45°−0°)) is a measure of the gloss, and as the value gets greater, it indicates that the gloss tends to be higher.

It has been found that, with regard to (C*(0°−45°)), when the value is in a little minus direction from around zero, although the reason for this is not clear, in a case in which the lightness L* has changed due to the unevenness of the face, the apparent change in gradation becomes better.

2. Sensorial Evaluation

The face of the same woman was made up by applying each of the powder foundations of Examples 1 to 11 and Comparative Examples 1 to 6 using a puff, and the face after makeup was visually observed, thereby performing sensorial evaluation. The evaluation method and the evaluation criteria are as follows.

—Evaluation Method and Evaluation Criteria—

In a room having, as the lighting, only one pair of two parallel fluorescent lamps arranged in a parallel configuration on the ceiling, the woman's face that had been put on makeup was placed at the backside of the room by 10° from the perpendicular direction of the center of the fluorescent lamp when seen from the observer side. The face of the woman was observed from the front direction and the change in gradation from the portion where the face was bright to the portion where the face was dark was evaluated into five grades (especially good, good, normal, slightly bad, and bad).

Further, the face of the woman was observed from the front direction and the gloss of the face was evaluated into three grades (low, middle, and high).

The results are shown in Table 2.

TABLE 2

| | L*45° | C*45° | angle h45° | C*(0-45°) | angle h*(0-45°) | L*(45°-0°) | Change in Gradation | Gloss |
|---|---|---|---|---|---|---|---|---|
| Example 1 | 78.2 | 20.4 | 69.1 | 1.2 | −1.3 | 6.4 | good | high |
| Example 2 | 82.0 | 18.4 | 67.8 | 0.5 | −0.2 | 9.3 | especially good | high |
| Example 3 | 78.8 | 21.6 | 68.9 | 0.5 | 0.5 | 6.9 | especially good | high |
| Example 4 | 80.6 | 22.2 | 69.0 | −0.1 | 0.6 | 8.2 | especially good | high |
| Example 5 | 78.0 | 21.3 | 70.0 | 1.2 | −0.7 | 6.4 | good | high |
| Example 6 | 77.3 | 21.4 | 71.8 | 1.1 | −0.7 | 7.6 | good | high |
| Example 7 | 77.9 | 21.4 | 69.1 | 1.1 | −0.2 | 6.9 | good | high |
| Example 8 | 79.6 | 20.2 | 68.3 | −0.2 | 0.2 | 6.3 | especially good | high |
| Example 9 | 79.0 | 18.2 | 68.4 | 0.6 | −0.1 | 6.9 | especially good | high |
| Example 10 | 78.6 | 20.7 | 68.1 | 2.0 | 0.5 | 9.0 | slightly good | high |

TABLE 2-continued

| | L*45° | C*45° | angle h45° | C*(0-45°) | angle h*(0-45°) | L*(45°-0°) | Change in Gradation | Gloss |
|---|---|---|---|---|---|---|---|---|
| Example 11 | 77.9 | 20.2 | 69.6 | 1.7 | −0.8 | 6.5 | slightly good | high |
| Comparative Example 1 | 76.1 | 20.6 | 69.5 | 2.3 | −1.8 | 6.1 | normal | low |
| Comparative Example 2 | 78.3 | 21.9 | 71.5 | 1.0 | −1.7 | 7.0 | slightly bad | high |
| Comparative Example 3 | 78.8 | 21.1 | 73.1 | 1.1 | −2.6 | 7.6 | normal | high |
| Comparative Example 4 | 78.3 | 20.8 | 62.5 | 1.9 | 3.7 | 8.3 | slightly bad | high |
| Comparative Example 5 | 79.7 | 17.0 | 69.9 | 2.4 | −2.1 | 7.1 | slightly bad | high |
| Comparative Example 6 | 78.4 | 20.1 | 70.7 | 3.8 | −2.5 | 9.0 | bad | high |

As shown in Table 2, it is understood that the foundations of Examples 1 to 11, which satisfied the relationship expressed by Formula (1) and the relationship expressed by Formula (2), exhibited good (smooth) change in gradation from the portion where the face was bright to the portion where the face was dark, and exhibited high gloss. Among the above, it is found that the foundations of Examples 1 to 9, which satisfied the relationship expressed by Formula (1') and the relationship expressed by Formula (2'), showed better results, and that the foundations of Examples 2 to 4, 8, and 9, which also satisfied the relationship expressed by Formula (1a) and the relationship expressed by Formula (2a), showed especially good results.

The disclosures of Japanese Patent Application No. 2010-075550 and Japanese Patent Application No. 2010-207214 are incorporated by reference herein in its entirety.

All publications, patent applications, and technical standards mentioned in this specification are herein incorporated by reference to the same extent as if such individual publication, patent application, or technical standard was specifically and individually indicated to be incorporated by reference.

The invention claimed is:

1. A base makeup cosmetic satisfying the relationship expressed by the following Formula (1) and the relationship expressed by the following Formula (2) and exhibiting a hue angle of the cosmetic in a range of from 60° to 80°:

$$(C*0)-(C*45)\leq 2.0 \quad \text{Formula (1)}$$

$$|(\text{angle } h*0)-(\text{angle } h*45)|\leq 1.5 \quad \text{Formula (2)}$$

wherein, when incident light falls on a light-receiving surface from a direction at −45° relative to the light-receiving surface, the light-receiving surface being a surface of a coating layer obtained by applying the base makeup cosmetic, (C*45) and (angle h*45) respectively represent the chroma (C*45) and hue angle (angle h*45) of reflected light in a specular reflection direction (a direction at 45°); and, when incident light falls on the light-receiving surface from a direction at −45° relative to the light-receiving surface, (C*0) and (angle h*0) respectively represent the chroma (C*0) and hue angle (angle h*0) of reflected light in a diffuse reflection direction (a direction at 0°), wherein the base makeup cosmetic comprises at least a colorant pigment, a pearl pigment, oil, and in a case of comprising an extender pigment, a hue angle of a mixture prepared using the extender pigment, the pearl pigment, and the oil is in a range of from 60° to 80°, and in a case of not comprising an extender pigment, a hue angle of a mixture prepared using the pearl pigment and the oil is in a range of from 60° to 80°; and a content of the pearl pigment is 7% by mass or more with respect to the total mass of the cosmetic; and the pearl pigment comprises a mixture of a gold pearl pigment and a red pearl pigment, and a mixture ratio of the gold pearl pigment to the red pearl pigment (the gold pearl pigment: the red pearl pigment) is from 1.5:1 to 4:1.

2. The base makeup cosmetic according to claim 1, satisfying the relationship expressed by the following Formula (1') and the relationship expressed by the following Formula (2'):

$$(C*0)-(C*45)\leq 1.5 \quad \text{Formula (1)}$$

$$|(\text{angle } h*0)-(\text{angle } h*45)|\leq 1.5 \quad \text{Formula (2)}.$$

3. The base makeup cosmetic according to claim 1, satisfying the relationship expressed by the following Formula (1a) and the relationship expressed by the following Formula (2a):

$$(C*0)-(C*45)\leq 1.0 \quad \text{Formula (1a)}$$

$$|(\text{angle } h*0)-(\text{angle } h*45)|\leq 1.0 \quad \text{Formula (2a)}.$$

4. The base makeup cosmetic according to claim 1, satisfying the relationship expressed by the following Formula (1b):

$$-5\leq (C*0)-(C*45)\leq 0 \quad \text{Formula (1b)}.$$

5. The base makeup cosmetic according to claim 1, satisfying the relationship expressed by the following Formula (1c):

$$|(C*0)-(C*45)|\leq 1.5 \quad \text{Formula (1c)}.$$

6. The base makeup cosmetic according to claim 1, satisfying the relationship expressed by the following Formula (3):

$$(L*45)-(L*0)\geq 5.0 \quad \text{Formula (3)}$$

wherein, when incident light falls on the light-receiving surface from a direction at −45° relative to the light-receiving surface, (L*45) and (L*0) respectively represent the lightness (L*45) of reflected light in the specular reflection direction (the direction at 45°), and the lightness (L*0) of reflected light in the diffuse reflection direction (the direction at 0°).

7. The base makeup cosmetic according to claim 1, wherein the extender pigment comprises at least one extender pigment selected from the group consisting of mica, sericite, and talc; the colorant pigment comprises at least one colorant pigment selected from the group consisting of yellow iron oxide, red iron oxide, black iron oxide, and titanium oxide;

and the pearl pigment comprises at least one pearl pigment selected from the group consisting of titanium oxide-coated mica, titanium oxide-coated glass flakes, and titanium oxide-coated talc.

8. The base makeup cosmetic according to claim 1, being a powder foundation, a liquid foundation, or a creamy foundation.

9. The base makeup cosmetic according to claim 1, wherein a content of the pearl pigment is 10% by mass or more with respect to the total mass of the cosmetic.

10. A base makeup cosmetic comprising at least a colorant pigment, a pearl pigment, an oil, and optionally an extender pigment, in which:
- in a case of comprising an extender pigment, a hue angle of a mixture prepared using the extender pigment, the pearl pigment, and the oil is in a range of from 60° to 80°, and in a case of not comprising an extender pigment, a hue angle of a mixture prepared using the pearl pigment and the oil is in a range of from 60° to 80°;
- a content of the pearl pigment is 7% by mass or more with respect to the total mass of the cosmetic; and
- the pearl pigment comprises a mixture of a gold pearl pigment and a red pearl pigment, and a mixture ratio of the gold pearl pigment to the red pearl pigment (the gold pearl pigment: the red pearl pigment) is from 1.5:1 to 4:1.

11. The base makeup cosmetic according to claim 10, wherein the extender pigment comprises at least one extender pigment selected from the group consisting of mica, sericite, and talc; the colorant pigment comprises at least one colorant pigment selected from the group consisting of yellow iron oxide, red iron oxide, black iron oxide, and titanium oxide; and the pearl pigment comprises at least one pearl pigment selected from the group consisting of titanium oxide-coated mica, titanium oxide-coated glass flakes, and titanium oxide-coated talc.

12. The base makeup cosmetic according to claim 10, wherein the base makeup cosmetic being one of a powder foundation, a liquid foundation, or a creamy foundation.

13. The base makeup cosmetic according to claim 10, wherein a content of the pearl pigment is 10% by mass or more with respect to the total mass of the cosmetic.

* * * * *